(12) United States Patent
Lehmann

(10) Patent No.: US 7,163,660 B2
(45) Date of Patent: Jan. 16, 2007

(54) ARRANGEMENT FOR TAKING UP LIQUID ANALYTES

(75) Inventor: Volker Lehmann, Munich (DE)

(73) Assignee: Infineon Technologies AG (DE)

( * ) Notice: Subject to any disclaimer, the term of this patent is extended or adjusted under 35 U.S.C. 154(b) by 0 days.

(21) Appl. No.: 09/867,830

(22) Filed: May 30, 2001

(65) Prior Publication Data

US 2002/0076353 A1  Jun. 20, 2002

(30) Foreign Application Priority Data

May 31, 2000 (DE) ............... 100 27 087

(51) Int. Cl.
- B01L 3/02 (2006.01)
- G01N 1/10 (2006.01)
- G01N 1/14 (2006.01)
- G01N 1/18 (2006.01)

(52) U.S. Cl. ............ 422/101; 422/100; 436/180; 436/168; 436/169; 436/175; 436/177; 436/178

(58) Field of Classification Search ......... 422/68.1, 422/99–104; 436/180, 168–169, 175, 177
See application file for complete search history.

(56) References Cited

U.S. PATENT DOCUMENTS

| | | | |
|---|---|---|---|
| 3,982,438 A | 9/1976 | Byrd | |
| 4,020,830 A | 5/1977 | Johnson et al. | |
| 4,087,248 A | 5/1978 | Miles | |
| 4,158,035 A | 6/1979 | Haase et al. | |
| 4,444,062 A | 4/1984 | Bennett et al. | |
| 4,461,328 A * | 7/1984 | Kenney | 141/67 |
| 4,511,534 A | 4/1985 | Bennett, Jr. et al. | |
| 4,532,805 A | 8/1985 | Flesher | |
| 5,000,921 A | 3/1991 | Hanaway et al. | |
| 5,171,537 A | 12/1992 | Wainwright et al. | |
| 5,174,162 A | 12/1992 | Miyake et al. | |
| 5,437,979 A | 8/1995 | Rampal et al. | |
| 5,545,531 A * | 8/1996 | Rava et al. | 435/6 |
| 5,843,767 A | 12/1998 | Beattie | |
| 5,895,631 A * | 4/1999 | Tajima | 422/101 |
| 5,915,284 A | 6/1999 | Meltzer et al. | |
| 6,830,717 B1 * | 12/2004 | Kopaciewicz et al. | 264/41 |
| 6,838,051 B1 * | 1/2005 | Marquiss et al. | 422/63 |
| 2002/0025582 A1 * | 2/2002 | Hubbard et al. | 436/180 |
| 2003/0108451 A1 * | 6/2003 | Su et al. | 422/100 |
| 2004/0018122 A1 * | 1/2004 | Micklash et al. | 422/130 |

(Continued)

FOREIGN PATENT DOCUMENTS

DE      43 10 607      10/1993

(Continued)

OTHER PUBLICATIONS

The Flow-Thru Chip™: A Three-Dimensional Biochip Platform, Adam Steel, et al (16 pages).

*Primary Examiner*—Brian R. Gordon
(74) *Attorney, Agent, or Firm*—Altera Law Group, LLC

(57) ABSTRACT

Apparatus for taking up liquid analytes having a microtitre plate with a plurality of wells and a plurality of pipettes, as well as a pump, which is coupled to several pipettes in such a way that an analytes can be simultaneously sucked out of several wells or introduced into several wells by actuating the pump.

10 Claims, 3 Drawing Sheets

U.S. PATENT DOCUMENTS

2004/0089330 A1 * 5/2004 Muller .................. 134/167 R

FOREIGN PATENT DOCUMENTS

| EP | 0215536 | 3/1987 |
| --- | --- | --- |
| EP | 0 810 438 | 12/1997 |
| EP | 0820811 | 1/1998 |
| WO | WO 86/03589 | 6/1986 |
| WO | WO 88/09201 | 12/1988 |
| WO | WO 95/11755 | 5/1995 |
| WO | WO 97/26539 | 7/1997 |
| WO | WO 98/26872 | 6/1998 |
| WO | WO 99/06148 | 2/1999 |
| WO | WO 00/02038 | 1/2000 |
| WO | WO 00/21666 | 4/2000 |

* cited by examiner

ARRANGEMENT FOR TAKING UP LIQUID ANALYTES

BACKGROUND OF THE INVENTION

The invention relates to an arrangement for taking up liquid analytes. Such an arrangement has a microtitre plate with a plurality of wells for taking up an analyte.

Such a microtitre plate is used, for example, for a wide variety of applications in medicine and biotechnology for taking up liquids to be analyzed, for example in the field of DNA analysis.

Usually, a different analyte to be analyzed is introduced in each well and via a pipette, usually via a plurality of adjacently arranged elements designed as a so-called pipette comb, the analyte is taken up; in a pipette comb, for example, a respective pipette is provided for each well in a row of the microtitre plate, which has wells arranged in an array.

By means of a pipette, an analyte is in each case withdrawn because of a reduced pressure created in the pipette, i.e., it is sucked up, from the corresponding well which is filled with the analyte and into which the pipette is dipped.

According to a known arrangement, the pipette is in each case coupled, via tubing, to a pump which is assigned uniquely to the respective pipette, and which produces the reduced pressure, in such a way that the analyte can be aspirated through the corresponding pipette by means of the pump and correspondingly can in turn be introduced into the well while being controlled by the pump.

Such a known microtitre plate has, for example, 96 wells with a size of 8 cm×12 cm.

Such a known microtitre plate, however, may in principle have any desired number of wells, usually up to 384.

A particular disadvantage of this known arrangement is that, because of the high number of pumps, it is impractical or sometimes impossible to provide a separate pump on such a small area of 8 cm×12 cm for each well in a row, i.e., for each of such a large number of pipettes.

The production of such a pipette comb, and hence of such an arrangement for taking up liquid analytes, is therefore very demanding and expensive.

It should furthermore be pointed out that, in the this known arrangement, a peristaltic pump is normally used in each case for aspirating the analyte out of the well in question and for introducing it therein.

A considerable disadvantage of this known arrangement is furthermore that a minimum amount of an analyte to be analyzed, of the order of 1 ml, is needed for the analysis.

Another disadvantage is that the large number of pumps required, with the associated tubing arrangement, is very complicated and therefore susceptible to faults.

Furthermore, U.S. Pat. Nos. 5,843,767 and 6,893,816, incorporated herein by reference, describe a Flow-Thru Chip™, by means of which analysis of the analyte with respect to the existence of biological material in the analyte is performed.

The Flow-Thru Chip™, which is a configuration of an analysis chip, has a plurality of channels through which the analyte is fed through the analysis chip, the surface of the channels being provided respectively with probe molecules, generally with molecules which can bind, preferably covalently, the correspondingly targeted biological material whose existence in the analyte is to be detected.

If the biological material in the analyte is a DNA strand with a predefined DNA sequence to be determined, then DNA probe molecules with a sequence complementary to the DNA sequence to be determined are applied to the surface of such a liquid channel in the Flow-Thru Chip™.

If the DNA material with the targeted DNA sequence is present in the analyte, then the DNA strands bind with the corresponding DNA probe molecules of opposite, i.e., complementary sequence.

In general, such an analysis chip is often used for the analysis, i.e., for the detection of macromolecular biopolymers, examples of which include proteins or peptides as well as DNA strands with a respective predefined frequency.

Furthermore, it is well known that it is possible to produce, from glass or silicon, a diaphragm which has a plurality of pores with a constant diameter of from 0.1 μm to 10 μm, and for example, from 0.1 μm to 1 μm.

It is therefore an object of the invention to provide an arrangement for taking up liquid analytes, in which even a large number of wells can be produced and operated in such an arrangement less expensively than is possible with an arrangement according to the prior art.

The object is achieved by the arrangement taking up liquid analytes having the features according to the independent patent claim.

An arrangement for taking up liquid analytes has a microtitre plate with a plurality of wells for taking up an analyte.

In the scope of the invention, a microtitre plate should be understood as being a plate having a plurality of wells for taking up an analyte, which usually have wells which are arranged in an array, i.e., in rows and columns with usually constant distances between them. It should be noted in this context, however, that a microtitre plate is not restricted to such an arrangement, but rather, in the scope of the invention, a microtitre plate should be understood as describing a structure having a plurality of arbitrarily arranged wells for taking up a liquid analyte.

One pipette is provided for a well, and in case of a plurality of wells, a plurality of pipettes are usually provided, a pipette being in each case usable to withdraw an analyte from an associated well, i.e., a well over which the pipette is currently arranged, or to introduce it into this well.

The arrangement has a pump which is coupled to several pipettes in such a way that an analyte can in each case be aspirated through an associated pipette by means of the pump, and analytes can be simultaneously aspirated out of several wells or introduced into several wells by actuating the pump.

In this way, the analytes can be aspirated using a very simple arrangement, in particular a significantly reduced number of pumps compared with the number of wells, for the case in which an analysis chip, for example the Flow-Thru Chip™, with probe molecules applied to the surfaces of the liquid channels, is provided in the suction path, i.e., in the liquid channel inside the pipette, to simultaneously analyze several analytes, which are usually different.

In this way, the overall arrangement can be produced and operated considerably less expensively.

Furthermore, the arrangement is considerably less complex and hence also considerably less prone to problems.

Analysis chips are furthermore provided for analyzing the analyte, one analysis chip being in each case assigned to a well in order to analyze an analyte introduced into the respective well. The surface of at least a part of the analysis chips, which surface comes into contact with the analyte, is designed in such a way the biological material for binding molecules contained in the analyte can be fixed on the surface.

This straightforwardly permits, for the first time, parallel analysis of biological material in a robust but nevertheless inexpensive and fast way.

The pipettes may be configured as a pipette comb.

According to another configuration of the invention, the pipette comb has a first element and a second element, which is coupled to the first element, the second element having the pipettes.

A plate may be arranged between the first element and the second element, the analysis chips for analyzing the analytes being arranged in this plate according to one configuration of the invention. One take-up well for analyzing an analyte introduced into the respective well is in each case usually provided for one analysis chip.

The surface of at least a part of the analysis chips, which surface comes into contact with the analyte, may have biological material so that it is possible to bind biological molecules, for example macromolecular biopolymers, contained in the analyte.

In the scope of this invention, macromolecular biopolymers should be understood as meaning, for example, proteins or peptides as well as DNA molecules.

According to one configuration of the invention, the microtitre plate has 96 wells or 384 wells for taking up a respective analyte.

An elastic diaphragm may in each case be sealingly arranged over at least some of the pipettes, so that the analyte can be sucked out of the corresponding well or introduced into the corresponding well by deforming the diaphragm.

Clearly, this configuration means that, by deforming the diaphragm, a reduced pressure or an overpressure can be produced in the pipette, i.e., between the diaphragm and the analyte in the pipette, it being possible to move the analyte inside the pipette, preferably through the analysis chip.

One advantage, when such a diaphragm is used, is that closed chambers are formed so the analytes cannot give off any vapours which may possibly be toxic to humans.

According to one configuration of the invention, a buffer plate is provided for each pipette, in order to mix the analyte supplied through the pipette, so the analysis result is improved further since, owing to the baffle plate in the flow path of the analyte, the mixing of the analyte and hence the contact of the analyte with the probe molecules on the surface of the liquid channels of the analysis chip is improved further.

Furthermore, according to one configuration of the invention, for the case in which temperature control is required in the arrangement, for example for chemical reactions or biological reactions, measuring elements and heating elements are provided in the arrangement.

These elements may be integrated in the analysis chip according to one configuration of the invention.

According to another configuration of the invention, the pump can be operated in such a way that the analyte is sucked by means of the reduced pressure produced in the pipette, which is less than an analyte surface tension possibly formed in the pipette.

This procedure utilizes the discovery that because of the capillary effect, especially at such small dimensions in a pipette for a microtitre plate, a very strong capillary effect is formed which leads to a very considerable surface tension on the analyte to be taken up, when all of the analyte has been sucked out of the well.

This approach prevents very straightforwardly, without any additional complex control means being required, air or another gas from being sucked into the pipette after all of the analyte has been taken up from the respective well.

This ensures that the amount of analyte, generally liquid and/or gas, which is taken up is always precisely the amount needed for the analysis.

Clearly, the invention consists in the fact that, by providing one pump for several pipettes and configuring them in such a way that different analytes can in each case be sucked simultaneously from several wells by means of one pump, and correspondingly analyzed, the complexity and the costs of an arrangement for taking up liquid analytes is improved considerably.

BRIEF DESCRIPTION OF THE DRAWINGS

Exemplary embodiments of the invention are represented in the figures and will be explained in more detail below.

DETAILED SPECIFICATION

First Exemplary Embodiment

Figure 1:
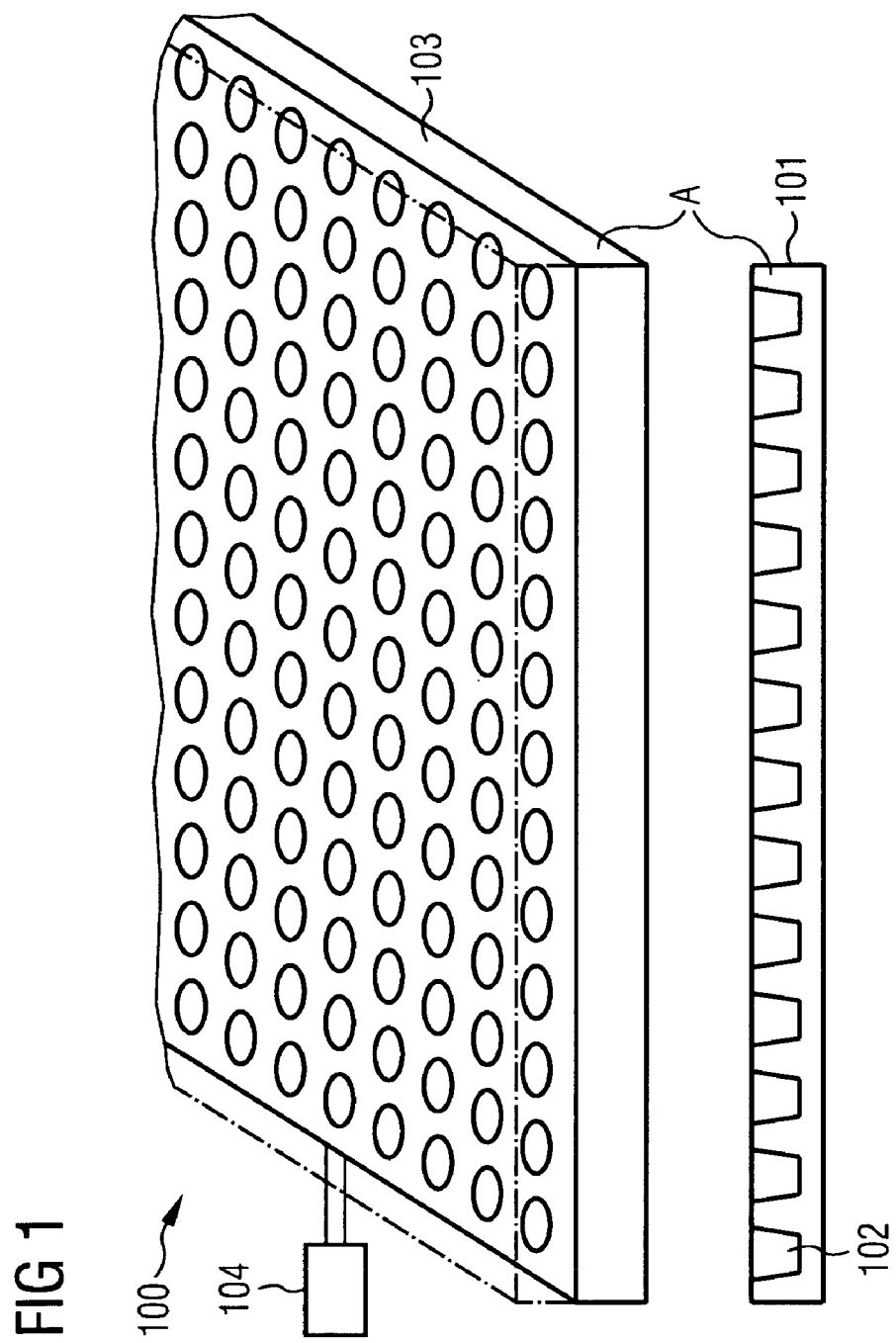
FIG. 1 shows a sketch of an arrangement for taking up liquid analytes according to a first exemplary embodiment of the invention.

FIG. 1 shows an arrangement 100 for taking up liquid analytes according to a first exemplary embodiment of the invention.

This arrangement 100 has a microtitre plate 101 with a plurality of wells 102 for taking up analytes, i.e. liquids to be analyzed, which are usually each different.

A further plate 103, which is coupled to the microtitre plate 101 by means of screws (not shown), is applied to the microtitre plate 101. The further plate 103 will be explained in more detail below.

Figure 2:
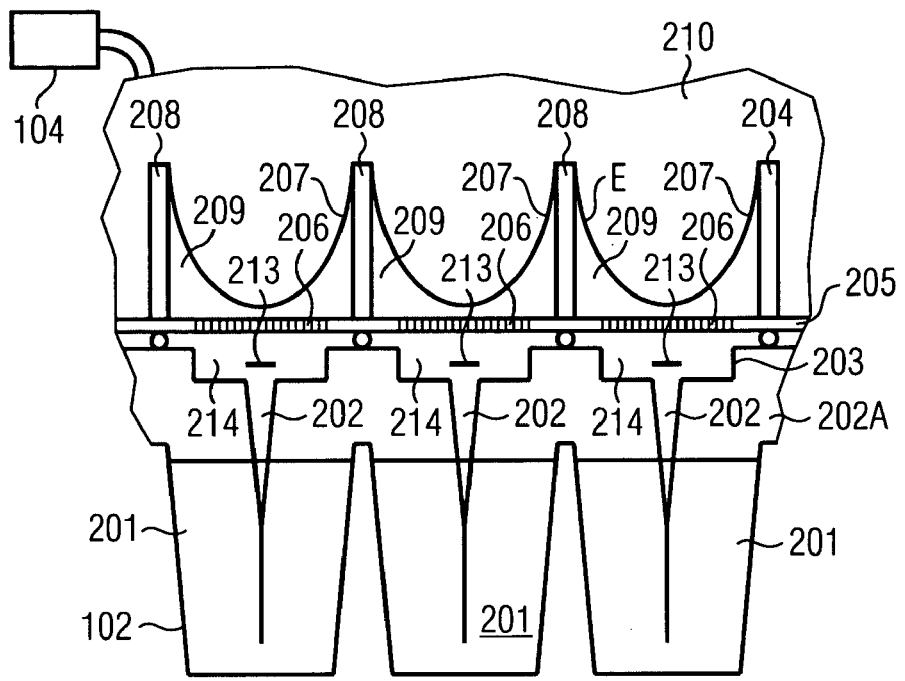
FIG. 2 shows a detail of the arrangement in FIG. 1 in cross section, in a state in which all of the analyte is located in the wells.

Via the further plate 103 which, corresponding to the wells 102, respectively has pipettes 202 and pipette comb 202A as presented in FIG. 2, a room 210 is formed which is hermetically coupled to a pump 104 which is applied to the further plate 103.

By means of the pump 104, it is possible to set the pressure inside the further plate 103, as described below, i.e., an overpressure or a reduced pressure can be freely set in the corresponding space 210 by the pump 104.

FIG. 2 shows an enlarged detail of circle 105 of the arrangement 100 in FIG. 1.

As can be seen from FIG. 2, an analyte 201 to be analyzed is usually introduced into each of the wells 102.

The pipettes 202 arranged in the further plate 103 are arranged in the further plate 103 in such a way that, when the further plate 103 is fastened on the microtitre plate 102 by means of the screws (not shown), a pipette 202 protrudes in each case into a well 102 assigned to it, and hence into the respective analyte 201.

The pipettes 202 are formed on a lower plastic body 203 of the further plate 103.

The lower plastic body 203 is coupled, for example adhesively bonded, to an upper plastic body 204.

According to this exemplary embodiment, an intermediate plate 205, in which of the analysis chips 206, according to this exemplary embodiment referred to as a Flow-Thru Chip™, and are fitted in such a way that a respective analysis chip 206 is provided for each well, is arranged between the lower plastic body 203 and the upper plastic body 204.

Clearly, this means that one analysis chip 206 is in each case intended to analyze one analyte 201, which is respectively contained in a well 102 and, according to a method described below, is sucked via the pipette 202 and the lower plastic body 203 through the analysis chip 206, i.e. through the liquid channels of the analysis chip 206, into the upper plastic body 204.

In this way, the analyte 201 is in each case brought into intimate contact with the probe molecules on the surface of the liquid channels of the analysis chip 206.

On the upper plastic body 204, a respective diaphragm 207 is provided for each well 102.

This means that the upper plastic body 204 in each case forms a space, essentially corresponding to the upper surface shape of the well 102, which is respectively formed by side walls 208 of the upper plastic body 204.

Clearly, chambers 209 are hence formed in the upper plastic body 204, which are in each case bounded by the walls 208, the diaphragm 207 and the intermediate plate 205 with the integrated analysis chip 206.

The diaphragm 207 is in each case an elastic diaphragm, for example made of latex, which can be modified by means of a pressure change in a space 210 which is located over the upper plastic body 204 and is coupled to the pump 104.

The space 210 may be filled with gas or with a liquid, the diaphragm being impermeable to the corresponding gas, or the liquid with which the space 210 is filled.

Clearly, a pressure variation in the space 210 hence deforms the diaphragm 207 so that a pressure variation is produced in the respective chambers 209, by means of which the analyte 201, via the pipette 202, is either sucked through the analysis chip 206 or discharged into the well.

The liquid channels in the Flow-Thru Chip™ 206 are coated with biological material, i.e. with DNA probe molecules according to this exemplary embodiment, which are bound to the surface of the liquid channels in the analysis chip 206 by means of the known gold/sulphur coupling.

If the analyte 201 to be analyzed has DNA strands with a sequence which is complementary to the DNA sequence of the DNA probe molecule, then these DNA strands bind covalently to the DNA probe molecules in the liquid channels of the analysis chip 206.

Figure 3:
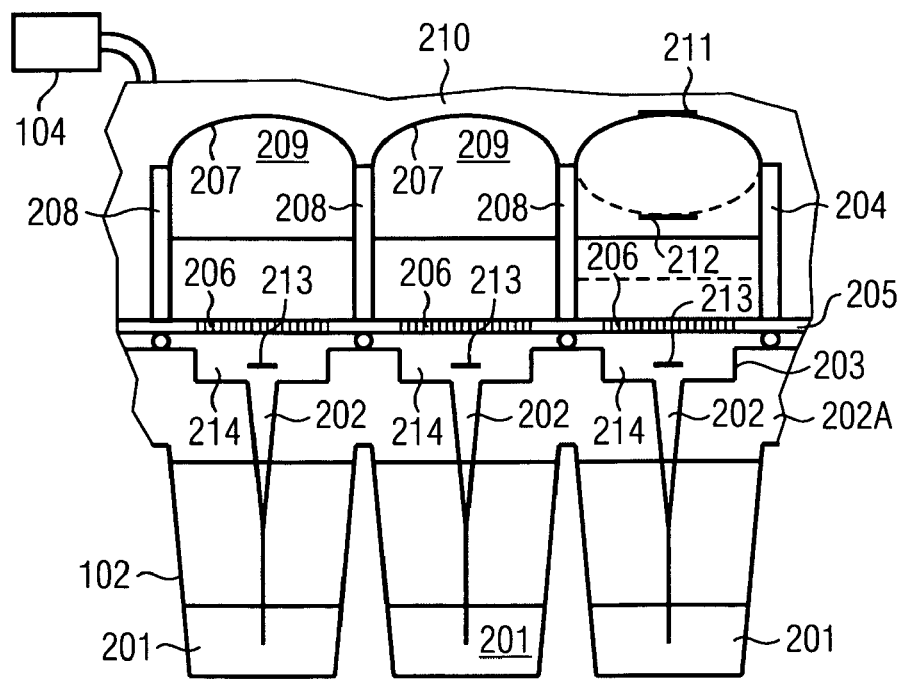
FIG. 3 shows a detail in FIG. 2, in the state such that some of the analytes have been sucked into a holding space by the pipettes.

Clearly, the diaphragm 207 is hence deformed in each case by a pressure change, as represented in FIG. 3, according to the size of the diaphragm between the two extreme positions (Arrow Heads G and H) symbolized in FIG. 3 by the tangents 211, 212 to the diaphragms which are in each case maximally curved.

Because of the deformation, as described above, the analyte is sucked in or released.

Furthermore, according to this exemplary embodiment, a buffer plate 213 which ensures improved mixing of the analyte 201 by the formation of a corresponding flow shape around the buffer plate 213, is provided in the lower plastic body 203 for each pipette 202, respectively between the pipette 202 and the intermediate plate 205.

According to this embodiment, it should be noted that the liquid amount of the analyte 201 pumped by means of the diaphragm 207 needs to be significantly greater than the volume, defined in each case for a pipette 202 by the lower plastic body 203, of a lower chamber 214 below the analysis chip 206.

After the analysis of the analyte has been carried out, which typically takes a few hours in the context of hybridization, the arrangement 100 is emptied using a maximum diaphragm setting in the position 212.

Rinsing procedures for the arrangement, using a rinsing solution, can be carried out in a similar way as for the analyzing.

Second Exemplary Embodiment

The second exemplary embodiment 400 corresponds essentially to the first exemplary embodiment, with the difference that no diaphragm 207 is needed.

In order to ensure that, after all of the analyte has been sucked up from a respective well, no air or another gas is sucked out of the well into the pipette, the pump 104 is operated in such a way that a surface tension, described below, which is formed in the analyte at the lower end of the respective pipette 202 is not exceeded.

Figure 4:
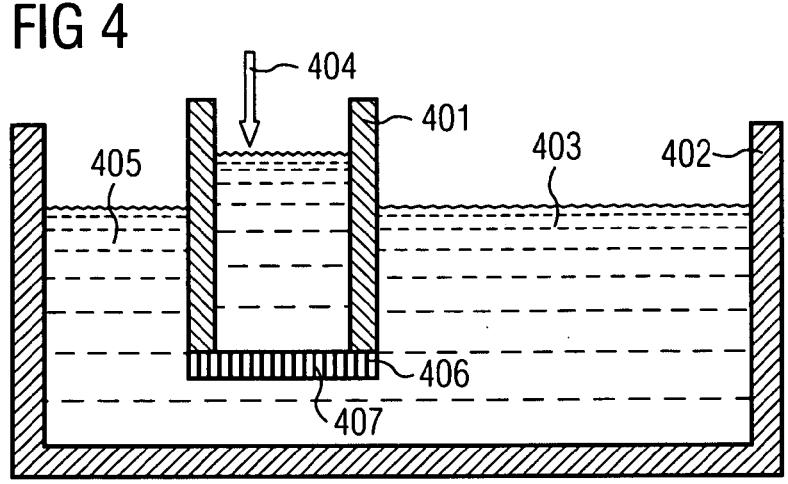
FIG. 4 shows a cross section through a pipette, which is used to illustrate a principle on which the second exemplary embodiment of the invention is based.

This principle is illustrated in FIG. 4.

FIG. 4 shows a pipette 401, which is dipped into a well 402 and thereby into the analyte 403.

A reduced pressure formed in the pipette 401 is symbolized in FIG. 4 by means of an arrow 404.

The pipette 401 according to this exemplary embodiment is configured as a tube with a diameter of approximately 1 cm and is sealed, for example adhesively bonded, at its lower end 405 to a diaphragm 406, the diaphragm 406 containing a plurality of pores 407, or at least one pore 407, with a preferably constant diameter, according to this exemplary embodiment a diameter of 10 µm.

In general, such a pore 407 may, for example, have a diameter of 0.1 µm to 100 µm.

A diaphragm 406 as disclosed by EP 0 296 348 B1, made of glass or silicon, is used according to this exemplary embodiment.

It is assumed according to this exemplary embodiment, without restricting the generality, that the diaphragm 406 is hydrophilically configured.

The analyte 403 then penetrates the pores 407 of the diaphragm 406 and can be sucked into the pipette 401 by a small reduced pressure, for example 0.03 bar according to this exemplary embodiment.

Figure 5:
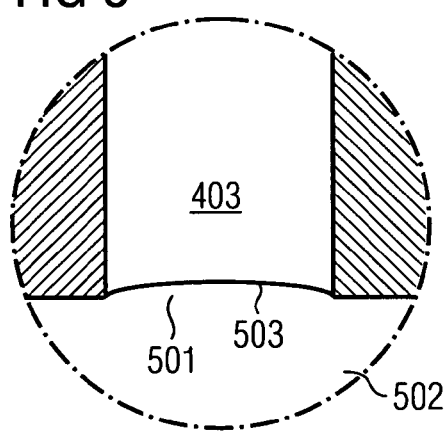
FIG. 5 shows a cross section through a pipette, which is used to illustrate a principle on which the second exemplary embodiment of the invention is based.

If the well 402 is emptied, i.e. the analyte 403 is taken up fully into the pipette 401, then a meniscus 503 is formed, as represented in FIG. 5 (enlarged circle marked V in FIG. 4), at each pore opening 501 between the analyte 403 and the air 502 which is all that remains in the well 402.

In order to deform the meniscus 503 which is being formed, in such a way that it is possible for air 502 to enter the pore 407, it is necessary to produce a substantially stronger reduced pressure than the reduced pressure which is required in order to such the analyte 403, in general a liquid, into the capillary, i.e. into the pipette 401.

This required pressure P can be estimated according to the following rule:

$$P = 2(s/r)$$

where
S denotes the surface tension of the respective liquid, i.e. of the analyte 403, and
r denotes the radius of the respective pore 407.

These values are usually known for a given arrangement.

If water is used as the analyte and a pore 407 has a radius of 10 μm, then a value of 0.29 bar is found for the required pressure P.

So that entry of air into the pore 407 can be prevented, it is necessary to ensure a pressure from the pump which is below this estimated pressure.

This control measure is usually noncritical since, as explained above, a reduced pressure of 0.03 bar is necessary in order to suck in the analyte, this pressure being an order of magnitude less than the critical pressure at which the surface tension would be overcome and air could enter the pore 407.

In other words, this means that the reduced pressure P produced in the pipette is in a range of 0.03<P<0.29 bar for this pipette with the dimensions stated above.

Entry of air into the pipette is hence prevented in a very simple way.

It is of course also possible, in the case of a hydrophobic diaphragm 407, similarly to pump a predefinable gas by means of the arrangement described above and to prevent entry of liquid through the respective pore, in general through a capillary.

Clearly, this exemplary embodiment makes it possible to ascertain automatedly whether all of the analyte 403 has been taken up from the respective well.

It is also automatedly ensured that no medium other than the material to be analyzed is taken up into the analysis device.

Figure 6:
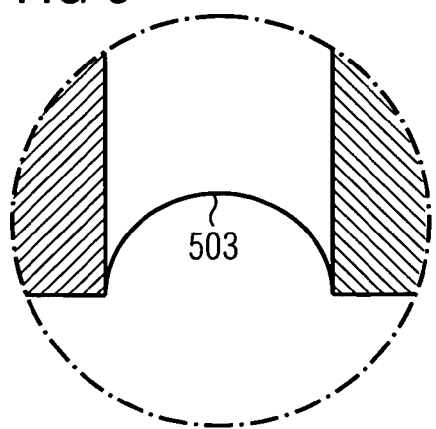
FIG. 6 shows a cross section through a pipette, which is used to illustrate a principle on which the second exemplary embodiment of the invention is based.

FIG. 6 shows the enlarged detail of a lower end of a pore 407 in FIG. 4 at a reduced pressure which lies in a range shortly before the air 502 enters the pore 407.

This is made clear by the strongly curved meniscus 503.

The invention claimed is:

1. An apparatus for aspirating and dispensing liquid analytes, comprising:
   a microtitre plate with a plurality of wells for holding an analyte therein
   a plurality of pipettes, corresponding with each well; by which an analyte can be withdrawn from said corresponding wells if the pipettes are immersed into the analyte of the corresponding wells;
   at least one pump, which is coupled to a plurality of said pipettes in such a way that an analyte in each well is transferred through corresponding pipette by means of the pump, wherein analytes can be simultaneously aspirated out of a plurality of said wells or introduced into a plurality of said wells by actuating the pump;
   a plurality of analysis chips arranged in an intermediate plate for analyzing the analyte and a plurality of corresponding chambers; and
   wherein said analysis chips correspond respectively with each well in order to analyze an analyte introduced into each respective well, wherein each analysis chip comprises a plurality of liquid channels, wherein each analysis chip is arranged between a respective chamber in a flow path of the analyte from a well into a pipette and into a chamber or from a chamber into a pipette and into a well; wherein the analyte is transferred through the liquid channels of the analysis chip into a chamber or out of a chamber, respectively, and wherein a portion of a surface area of the liquid channels of the analysis chips comes into contact with the analyte, said surface area is constructed to allow biological material for binding molecules contained in the analyte to be fixed thereon.

2. The apparatus according to claim 1, further comprising upper bodies coupled to lower bodies, the lower bodies comprising the pipettes, wherein the intermediate plate is arranged between the upper bodies and the lower bodies.

3. The apparatus according to claim 1, wherein a portion of the surface of the liquid channels that comes into contact with the analyte, further comprises biological material for binding molecules contained in the analyte.

4. The apparatus according to claim 1, wherein the microtitre plate comprises 96 wells or 384 wells.

5. The apparatus according to claim 1, further comprising an elastic, pump-diaphragm is arranged over at least one of the pipettes, so that an analyte can be aspirated out of the corresponding well or introduced into the corresponding well by deforming the diaphragm.

6. The apparatus according to claim 1, in which a buffer plate is provided for each pipette, in order to mix the analyte delivered by the pipette.

7. An apparatus for analyzing an analyte, comprising:
   a microtitre plate having a plurality of wells;
   a plurality of pipettes;
   a plurality of analysis chips, each analysis chip comprising a plurality of channels containing probe molecules for analyzing the analyte, and being located between one well of said plurality of wells and with one pipette of said plurality of pipettes; and
   a pumping means for passing the analyte through the channels of the analysis chips, thereby contacting the probe molecules, by extracting the analyte from or introducing the analyte, through the pipettes, into the wells.

8. The apparatus according to claim 7, wherein the probe molecules of the analysis chips are macromolecular biopolymers.

9. The apparatus according to claim 7, further comprising a plurality of buffer plates in the flow path of the analyte for improving the contact between the analyte and the probe molecules of the analysis chips.

10. The apparatus according to claim 7, further comprising a plate on which the plurality of analysis chips are fitted.

* * * * *